(12) United States Patent
Bendall

(10) Patent No.: US 6,830,545 B2
(45) Date of Patent: Dec. 14, 2004

(54) TUBE GRIPPER INTEGRAL WITH CONTROLLER FOR ENDOSCOPE OF BORESCOPE

(75) Inventor: Clark A. Bendall, Syracuse, NY (US)

(73) Assignee: Everest VIT, Flanders, NJ (US)

( * ) Notice: Subject to any disclaimer, the term of this patent is extended or adjusted under 35 U.S.C. 154(b) by 282 days.

(21) Appl. No.: 10/144,503

(22) Filed: May 13, 2002

(65) Prior Publication Data

US 2003/0212308 A1 Nov. 13, 2003

(51) Int. Cl.[7] ................................................. A61B 1/00
(52) U.S. Cl. ...................................... 600/114; 600/102
(58) Field of Search ................................ 600/101, 102, 600/114, 131

(56) References Cited

U.S. PATENT DOCUMENTS

| | | | |
|---|---|---|---|
| 3,690,775 A | | 9/1972 | Cousins |
| 3,822,697 A | * | 7/1974 | Komiya ........................ 600/114 |
| 4,011,017 A | | 3/1977 | Feuerstein et al. |
| 4,078,864 A | | 3/1978 | Howell |
| 4,108,554 A | | 8/1978 | Joyce |
| 4,550,715 A | | 11/1985 | Santangelo et al. |
| 4,765,314 A | * | 8/1988 | Kolditz et al. ............... 600/114 |
| 4,972,827 A | * | 11/1990 | Kishi et al. ............. 604/164.09 |
| 5,280,781 A | * | 1/1994 | Oku .............................. 600/114 |
| 5,373,317 A | | 12/1994 | Salvati et al. |
| 5,545,200 A | | 8/1996 | West et al. |
| 5,575,754 A | | 11/1996 | Konomura |
| 5,782,749 A | | 7/1998 | Riza |
| 5,801,825 A | | 9/1998 | Nutter et al. |
| 5,882,333 A | | 3/1999 | Schaer et al. |
| 5,904,667 A | | 5/1999 | Falwell |
| 5,941,815 A | * | 8/1999 | Chang ........................ 600/114 |
| 5,954,654 A | | 9/1999 | Eaton et al. |
| 6,156,027 A | | 12/2000 | West |
| 6,169,916 B1 | | 1/2001 | West |
| 6,171,234 B1 | | 1/2001 | White et al. |
| 6,293,908 B1 | * | 9/2001 | Fujikura et al. ............ 600/114 |
| 6,358,199 B1 | | 3/2002 | Pauker et al. |
| 6,432,046 B1 | | 8/2002 | Yarush et al. |
| 6,464,645 B1 | | 10/2002 | Park et al. |
| 6,471,638 B1 | | 10/2002 | Chang et al. |
| 2001/0037084 A1 | | 11/2001 | Nardeo |
| 2002/0120178 A1 | | 8/2002 | Tartaglia et al. |

FOREIGN PATENT DOCUMENTS

| | | |
|---|---|---|
| JP | 09056665 | 3/1997 |
| JP | 11076403 | 3/1999 |
| WO | WO 96/01592 | 1/1996 |

* cited by examiner

Primary Examiner—Beverly M. Flanagan
(74) Attorney, Agent, or Firm—Wall Marjama & Bilinski LLP

(57) ABSTRACT

A probe controller is integral with a gripper for the probe's insertion tube. The gripper is easily operated with one hand, permitting a user to hold, release, and insert the insertion tube with the same hand that operates the controls on the controller, thus freeing the user's other hand to feed the insertion tube into the opening, perform other operations, or optionally to operate the controls.

23 Claims, 2 Drawing Sheets

TUBE GRIPPER INTEGRAL WITH CONTROLLER FOR ENDOSCOPE OF BORESCOPE

FIELD OF THE INVENTION

This invention relates generally to the field of endoscope/borescope controllers, and more particularly to a tube gripper integral with a controller for an endoscope/borescope.

BACKGROUND OF THE INVENTION

Video endoscopes or borescopes, hereinafter referred to as probes, generally have a flexible insertion tube with a diameter of one inch or less. The tube is usually pushed into inaccessible areas so they can be visually inspected. Feeding the insertion tube into an area is difficult with one hand as the tube tends to slide out of the area of interest when it is released. One hand is often used to hold the position of the insertion tube steady as the other hand moves down the tube in preparation for the next push. Most video probes also have a control section which has controls for articulating the tip of the probe as well as buttons for activating other system functions. Control sections of this type are disclosed, for example, in U.S. Pat. No. 5,373,317 to Salvati et al. These control sections are hand-held units that include a console having a joystick or similar user-actuable means that is interconnected to contained servo or stepper motors to articulation cables that can control the movement of the distal bending section of the insertion tube (e.g., the probe). Additionally, an electronic control circuit, also within the housing of the control unit, which can include a microprocessor is provided. This control circuit is interconnected to the joystick or trackball as well as to at least one user-actuable button or key switch in order to control aspects of the video probe such as to image freeze or capture modes, brightness, image manipulation and the like relative to an integral display screen. This control circuit can also control a cursor and cursor movement on the screen relating to movement of the probe. Additional control circuitry can be contained in a remote unit or within the hand-held control section. Presently, it is difficult for the user to hold and/or use a control section, as described above, while pushing the insertion tube.

SUMMARY OF THE INVENTION

Briefly stated, a probe controller is integral with a gripper for the probes's insertion tube. The gripper is easily operated with one hand, permitting a user to hold, release, and insert the insertion tube with the same hand that operates the controls on the controller, thus freeing the user's other hand to feed the insertion tube into the opening, perform other operations, or optionally to operate the controls.

According to an embodiment of the invention, a tube gripper for a probe includes a tube channel running lengthwise through the tube gripper for receiving an insertion tube of the probe; control means, integral with the tube gripper, for controlling at least one function of the probe; and gripping means for frictionally connecting the tube gripper to the insertion tube.

DETAILED DESCRIPTION OF THE PREFERRED EMBODIMENT

Figure 1:
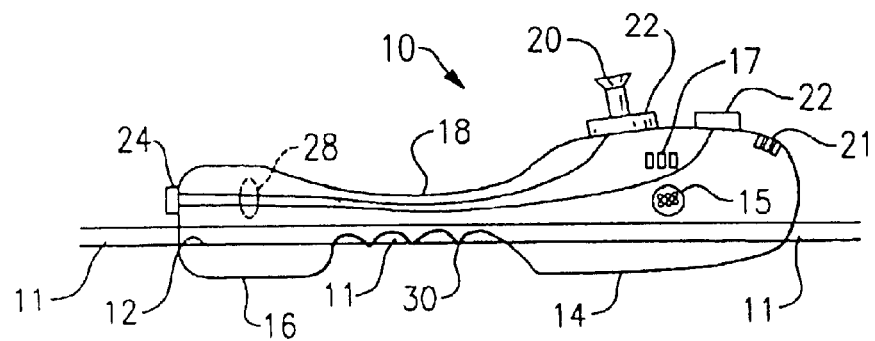
FIG. 1 shows a side cross-sectional view of an embodiment of the invention.
Figure 2:
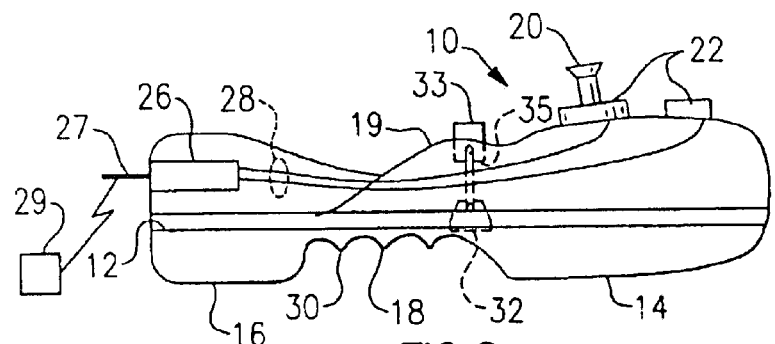
FIG. 2 shows a side cross-sectional view of an embodiment of the invention.

Referring to FIGS. 1–2, an embodiment of an insertion tube gripper 10 includes a tube channel 12 running throughout its length. Tube channel 12 is preferably sized to accommodate a typical insertion tube 11 of a probe. A front portion 14 of tube gripper 10 contains various probe controls such as a joystick 20 and control buttons 22. Other possible controls include a track ball, mouse, touch screen, etc. A rear portion 16 of tube gripper 10 optionally includes a wired connection 24 to a probe base station 29. Alternatively, rear portion 16 contains a small radio transceiver 26 with an antenna 27 for wireless communication to probe base station 29. Connector 24 or transceiver 26 is preferably connected to a joystick 20 and control buttons 22 via a cable or cables 28. Power may be provided to the probe controls via wired connection 24 or using a battery.

Insertion tube 11 only carries the raw video signal from the imager of the probe to base station 29. The viewable video is sent from base station 29 to the probe controls either via RF or wired link in either analog or digital format.

Functions and settings controlled by joystick 20 may include articulation of the tip of the endoscope, menu navigation, text entry, image panning, image selection, cursor positioning, text positioning, zoom level, illumination level, image brightness control, or other such functions. Control buttons 22 may provide any of the possible joystick-controlled functions plus others such as controlling image inversion, image storage/recall, enter/cancel functions, articulation mode changes, video switching control, measurement initiation/selection, operating mode selection and the like. Joystick 20 may also include an integral pushbutton which may provide any of the control-button functions. Another control mechanism may be used in place of joystick 20 such as a mouse pad or track ball. A single board preferably located in the joystick/button area would preferably hold the control mechanisms, such as joystick 20 and control buttons 22, as well as transceiver 26 and a microprocessor (not shown) if desired.

A middle portion 18 of tube gripper 10 is preferably shaped to accommodate a user's hand, with a molded portion 30 conforming to the user's fingers as they are wrapped around tube gripper 10. In middle portion 18, tube channel 12 is exposed to the outside so that at least one of the user's fingers or thumbs grips insertion tube 11 directly. The user then slides tube gripper 10 up and down insertion tube 11 as desired.

An optional video display connector 15 permits attaching a video display 40 (FIGS. 5–7), thus allowing video display 40 to be located near the user and connected via a cable to tube gripper 10 such that the cable need not be run back to probe base station 29. Connector 15 could attach in a number of places including the front end near the control buttons, the rear, or to the side. An optional microphone 21 permits comment recording and voice control. An optional speaker 17 permits playback of comments and/or button activation feedback.

Referring to FIG. 2, in an alternate embodiment, tube channel 12 is not exposed to the outside in middle portion 18, but a mechanical gripping mechanism 32, located in middle portion 18 or front portion 14, is connected to a thumb trigger 33 by a mechanical linkage 35. Depressing thumb trigger 33 causes gripping mechanism 32 to clamp onto insertion tube 11. Alternately, releasing thumb trigger 33 causes gripping mechanism 32 to release insertion tube 11. Gripping mechanism 32 may also be designed such that depressing thumb trigger 33 releases insertion tube 11, and releasing thumb trigger 33 causes gripping mechanism 32 to clamp onto insertion tube 11. Molded portion 30 optionally includes a thumb rest 19.

Figure 3:
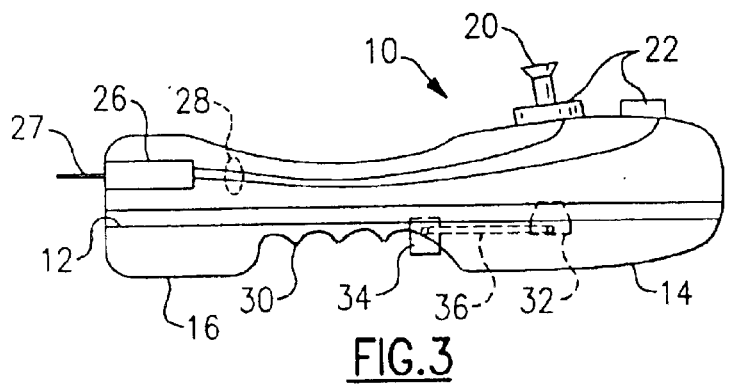
FIG. 3 shows a side cross-sectional view of an embodiment of the invention.

Referring to FIG. 3, in another embodiment similar to the embodiment of FIG. 2, tube channel 12 is not exposed to the outside in middle portion 18, but a mechanical gripping mechanism 32, preferably located in front portion 14, is connected to a finger trigger 34 by a mechanical linkage 36. Depressing finger trigger 34 causes gripping mechanism 32 to clamp onto insertion tube 11. Alternately, releasing finger trigger 34 causes gripping mechanism 32 to release insertion tube 11. Mechanical linkage 36 is optionally located in rear portion 16 of tube gripper 10. Gripping mechanism 32 may also be designed such that depressing finger trigger 34 releases insertion tube 11, and releasing finger trigger 34 causes gripping mechanism 32 to clamp onto insertion tube 11.

Figure 4:
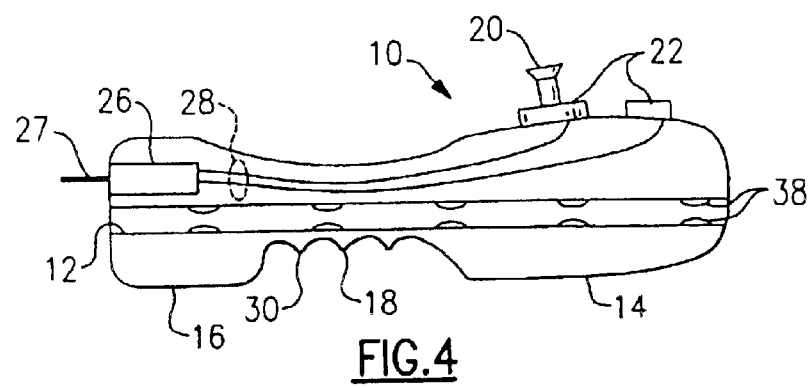
FIG. 4 shows a side cross-sectional view of an embodiment of the invention.

Referring to FIG. 4, another embodiment has neither an exposed tube channel nor a finger trigger. Instead, fixed or adjustable friction applicators 38 are located within tube channel 12 which provide steady friction between tube gripper 10 and insertion tube 11. Friction applicators could be small brushes or other materials which have a lower sliding coefficient of friction than static coefficient of friction.

Figure 5:
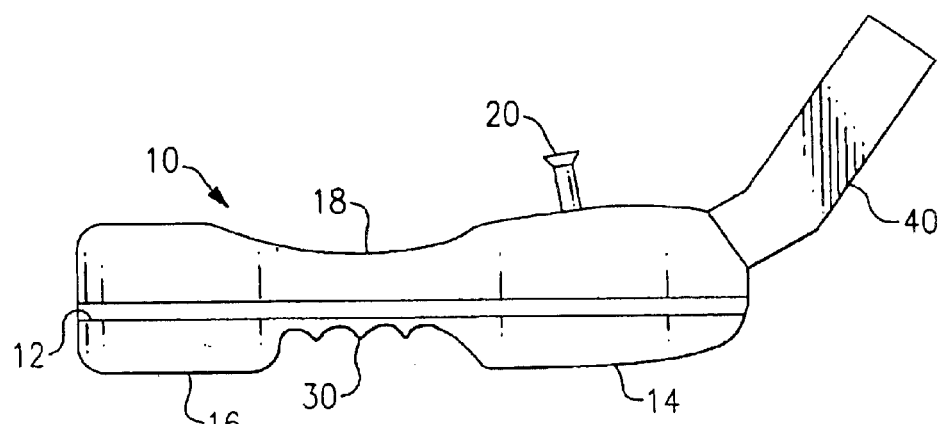
FIG. 5 shows a side view of an embodiment of the invention with a display mounted on a front portion thereof.
Figure 6:
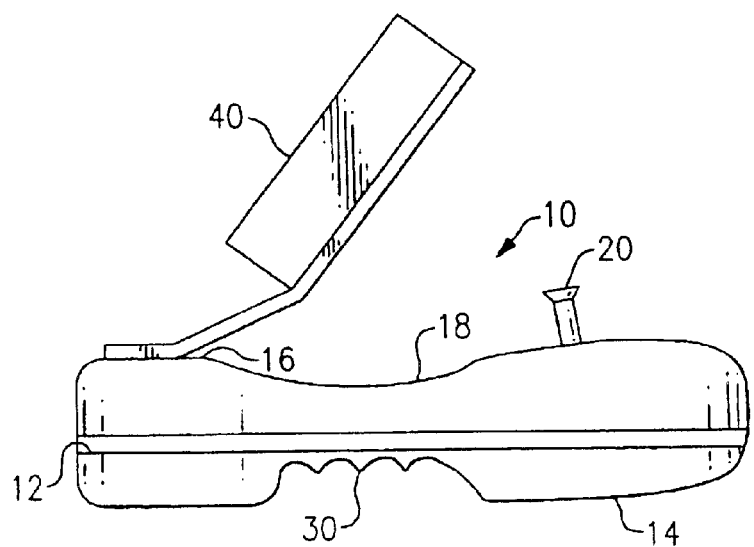
FIG. 6 shows a side view of an embodiment of the invention with a display mounted on a rear portion thereof.
Figure 7:
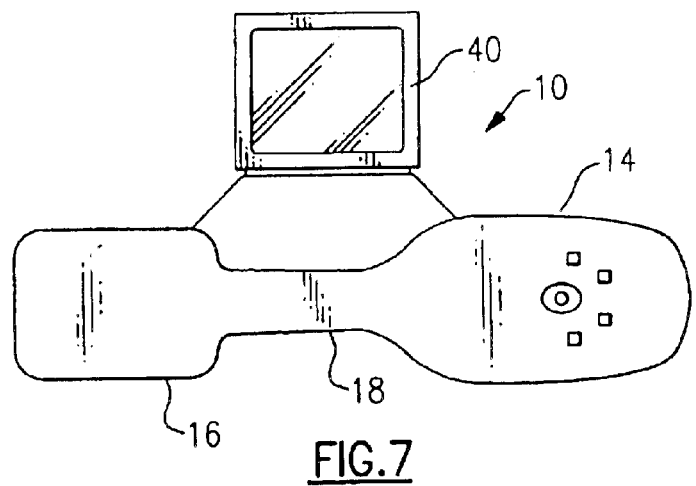
FIG. 7 shows a top view of an embodiment of the invention with a display mounted on a side portion thereof.

Referring to FIG. 5, a display 40 is shown mounted on front portion 14 of tube gripper 10. In FIG. 6, display 40 is shown mounted on rear portion 16 of tube gripper 10. In FIG. 7, display 40 is shown side mounted onto tube gripper 10. The purpose of these different mounting positions is so that display 40 is in the same vicinity as the controls, so that users don't have to turn their head/body to look from the controls to display 40. The controls and display 40 can also be close to the port through which the probe is inserted to further reduce head/eye/body movement.

In the embodiments of FIGS. 1–7, channel 12 of tube gripper 10 optionally opens along a seam on the underside of tube gripper 10 which allows the user to clamp tube gripper 10 onto insertion tube 11. Tube channel 12 may require that insertion tube 11 be inserted from the front or rear of the device. Alternatively, an access panel may be provided which, when opened, allows insertion tube 11 to be placed in tube channel 12 at any point along insertion tube 11. Tube channel 12 may also contain flexible or movable components between the tube channel itself and the bottom side of the gripper/controller through which insertion tube 11 may be forced to place insertion tube 11 in tube channel 12 thus allowing the gripper/controller to be attached to insertion tube 11 at any point.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. A tube gripper for an endoscopic apparatus, comprising:
    a hand-held control unit, said hand-held control unit including at least one user-actuable control feature for controlling at least one function of said probe;
    a tube channel running lengthwise through the interior of said hand-held control unit and sized for receiving an insertion tube of said endoscopic apparatus; and
    gripping means disposed within said hand-held control unit for frictionally connecting said tube channel to said insertion tube.

2. A tube gripper according to claim 1, wherein said one user-actuable control feature includes at least one of a joystick and a trackball disposed on the exterior of said hand-held control unit.

3. A tube gripper according to claim 2, further comprising means for connecting said at least one user-actuable control feature to a probe base unit.

4. A tube gripper according to claim 3, wherein said means for connecting includes a cable.

5. A tube gripper according to claim 3, wherein said means for connecting includes means for wireless data transfer between said at least one user-actuable control feature and said base unit.

6. A tube gripper according to claim 1, wherein said gripping means comprises an opening in a middle portion of said control unit such that said tube channel is exposed such that at least one finger of a user frictionally connects said tube channel to said insertion tube.

7. A tube gripper according to claim 1, wherein said gripping means comprises:
    a mechanical gripping mechanism inside said control unit; and
    one of a finger and thumb trigger mechanically linked to said gripping mechanism such that pressing said one of said finger and thumb trigger frictionally connects said tube channel to said insertion tube.

8. A tube gripper according to claim 7, wherein said mechanical gripping mechanism is disposed in a front portion of said control unit.

9. A tube gripper according to claim 7, wherein said mechanical gripping mechanism is disposed in a middle portion of said control unit.

10. A tube gripper according to claim 1, wherein said gripping means comprises:
    a mechanical gripping mechanism inside said control unit; and
    one of a finger and thumb trigger mechanically linked to said gripping mechanism such that releasing said one of a finger and thumb trigger frictionally connects said tube channel to said insertion tube.

11. A tube gripper according to claim 10, wherein said mechanical gripping mechanism is disposed in a front portion of said control unit.

12. A tube gripper according to claim 10, wherein said mechanical gripping mechanism is disposed in a middle portion of said control unit.

13. A tube gripper according to claim 1, wherein a middle portion of said control unit is shaped to conform to a hand grip of a user.

14. A tube gripper according to claim 1, wherein said gripping means includes a material affixed to an inside of said tube channel which has a lower sliding coefficient of friction than a static coefficient of friction.

15. A tube gripper according to claim 1, further comprising a video display detachably mounted on said hand-held control unit.

16. A tube gripper according to claim 1, wherein said tube channel receives said insertion tube only through an end of said tube channel.

17. A rube gripper according to claim 1, wherein said tube channel receives said insertion tube through a lengthwise slit in said tube channel.

18. A tube gripper according to claim 1, further comprising a movable panel which permits said insertion tube to be placed in said tube channel at any point along said insertion tube.

19. A tube gripper according to claim 1, further comprising a displaceable barrier along an underside of said tube channel such that said insertion tube may be forced past a displaceable barrier into said tube channel at any point along said insertion tube.

20. A tube gripper according to claim 1, further comprising a video display connector on said hand-held control unit.

21. A tube gripper according to claim 1, further comprising a microphone disposed within said hand-held control unit.

22. A tube gripper according to claim 1, further comprising a loudspeaker disposed within said hand-held control unit.

23. A tube gripper according to claim 1, wherein said user-actuable control feature includes at least one of a key switch and a button disposed on the exterior of said hand-held control unit.

* * * * *

UNITED STATES PATENT AND TRADEMARK OFFICE
CERTIFICATE OF CORRECTION

PATENT NO. : 6,830,545 B2
DATED : December 14, 2004
INVENTOR(S) : Clark A. Bendall It is certified that error appears in the above-identified patent and that said Letters Patent is hereby corrected as shown below:

Column 5,
Line 9, the word "rube" is incorrect please replace with the word -- tube --.

Signed and Sealed this

Fifth Day of April, 2005

JON W. DUDAS
*Director of the United States Patent and Trademark Office*